United States Patent [19]

Shibanai

[11] Patent Number: 4,725,657

[45] Date of Patent: Feb. 16, 1988

[54] SYNTHETIC RESIN PRODUCT CONTAINING COMPOUND INCLUDED IN CYCLODEXTRIN AND PROCESS FOR THE PRODUCTION OF THE SAME

[75] Inventor: Ichiro Shibanai, Tokyo, Japan

[73] Assignee: Japan Liquid Crystal Co., Ltd., Tokyo, Japan

[21] Appl. No.: 915,176

[22] Filed: Oct. 3, 1986

Related U.S. Application Data

[62] Division of Ser. No. 809,081, Dec. 12, 1985, abandoned.

[30] Foreign Application Priority Data

Dec. 27, 1984 [JP]  Japan ................................. 59-274133

[51] Int. Cl.$^4$ ..................... A61K 7/46; C08G 18/00
[52] U.S. Cl. ..................................... 523/210; 524/27; 524/58; 523/122; 512/4
[58] Field of Search ............. 527/300, 313; 524/58, 524/27; 252/522 R, 389 R; 523/122

[56] References Cited

U.S. PATENT DOCUMENTS 3,061,444  10/1962  Rogers et al. ....................... 536/103
3,420,788  1/1969   Solms ................................. 527/300
4,356,115  10/1982  Shibanai et al. ................. 252/522 A

FOREIGN PATENT DOCUMENTS 8150577  9/1983  Japan.

*Primary Examiner*—Delbert R. Phillips
*Assistant Examiner*—Nathan M. Nutter
*Attorney, Agent, or Firm*—Burgess, Ryan & Wayne

[57] ABSTRACT

A synthetic resin product which contains various substances such as perfumes, insectifuges/insecticides, rust preventives, mold/mildes-proofing or anti-fungi agents which are inactivated by forming an inclusion compound thereof in cyclodextrin and coated with glycitol(s) to thereby prolong the duration period thereof. A process for the production of the same is further disclosed.

9 Claims, No Drawings

SYNTHETIC RESIN PRODUCT CONTAINING COMPOUND INCLUDED IN CYCLODEXTRIN AND PROCESS FOR THE PRODUCTION OF THE SAME

This is a division of application Ser. No. 809,081, filed Dec. 12, 1985, abandoned.

BACKGROUND OF THE INVENTION

1. Field of the Invention

This invention relates to a synthetic resin product containing various substance(s) selected from among perfumes, insectifuges, rust preventive, mildewproofing agent and bactericide in the form of an inclusion compound in cyclodextrin and a process for the production of the same.

2. Description of the Prior Art

There have been developed various processes for the production of smelling and/or insectifugal synthetic resin products. Some processes comprise applying perfume(s) and/or insectifuge(s)/insecticide onto the surface of a synthetic resin product. Others comprise injecting perfume(s) and/or insectifuge(s)/insecticide into a space in a synthetic resin product or laminating synthetic resin sheets and injecting perfumes(s) and/or insectifuge(s)/insecticide between these sheets. It is also possible to mix perfume(s) and/or insectifuge(s)/insecticide with a synthetic resin compound followed by molding the obtained mixture. Perfume(s) and/or insectifuge(s)/insecticide applied on the surface of a synthetic resin product would vaporize so soon that they might not exhibit a persistent effect. On the contrary, those injected into a synthetic resin product would hardly vaporise and might not exhibit an expected effect. Further direct addition of perfume(s) and/or insectifuge(s)/insecticide to a synthetic resin compound is not as effective as it seems. This is because perfumes and/or insectifuges/insecticides are generally so volatile, liable to denature and unstable to heat that it is difficult in practice to mold a mixture of perfume(s) and/or insectifuge(s)/insecticides and a synthetic resin compound into a desired shape. It was further attempted to adsorb desired perfume(s) and/or insectifuge(s)/insecticide(s) by porous inorganic substances such as calcium silicate, zeolite or powdery alumina or porous polymer powders obtained by quenching and artificially grinding synthetic resins with the use of liquid nitrogen during the preparation thereof and to incorporate the obtained composition in a plastic followed by molding. However the desired perfume(s) and/or insectifuge(s)/insecticide(s) are adsorbed merely in pores in each process so that it is necessary to adsorb an excessive amount of them, including those which vaporize at the molding temperature, to give a sufficient amount of the same in molded products, which brings about an additional cost. Thus these processes are not preferable. Further perfume(s) and/or insectifuge(s)/insecticide(s) are not chemically bonded to cyclodextrin but merely absorbed in pores. Therefore some might be completely removed when heated for molding or might bleed in a short period. Thus these processes are not practical.

Under these circumstances, we have previously invented a process for producing a smelling synthetic resin product which comprises forming an inclusion compound consisting of a perfume included in cyclodextrin, drying and powdering the obtained inclusion compound and mixing the obtained powder with a synthetic resin compound (cf. Japanese Pat. No. 1090861).

We have further invented a process for producing an insectifugal and insecticidal film which comprises forming an inclusion compound consisting of an insectifugal and insecticidal agent included in cyclodextrin, drying and powdering the obtained inclusion compound and mixing the obtained powder with a synthetic resin compound followed by molding into a film (cf. Japanese Patent Application No. 188212/1984).

Machines as well as their parts have been packaged by applying rust preventives such as liquid paraffin thereon to warp them with oil membrane to thereby prevent rusting. The rust preventives such as liquid paraffin are removed at use. Therefore it is required to apply a rust preventive and to remove the same each time a machine is packaged. Conventional oilpapers exhibit some rust preventive effect. However this effect is so insufficient that it is necessary to directly apply a rust preventive on a machine to be packaged. It has been also attempted to package a machine with a paper impregnated with a rust preventive. However this method is available only in a limited range since fine paper pieces entering apertures of a precision machine would cause trouble.

It is a large problem to prevent rust or mildew in silicone and epoxy resins which have been recently employed in semiconductor materials. Since these resins are used in precision electrical instruments, it is impossible to spray or apply rust preventive(s) or mildewproofing agent(s) thereon. Thus these materials are packaged with paper sheets exhibiting a rust preventive and/or mildew-proofing effect.

Also it is sometimes required to prevent rusting in coatings, tackifiers and adhesives. Furthermore those products having a smell or an insectifugal and/or rust preventive effect may be available in a wider range. We have previously invented a product wherein an inclusion compound consisting of a perfume included in cyclodextrin is formed, the inclusion compound thus obtained is mixed with a latex and the mixture is applied on the surface of a tacky substrate (cf. Japanese Patent Laid-Open No. 185372/1982).

A smelling synthetic resin product produced by forming an inclusion compound consisting of a perfume included in cyclodextrin, powdering and drying the obtained inclusion compound and mixing the obtained powder with a synthetic resin compound is much more excellent than those produced by conventional methods. Subsequent studies have proved that not only perfumes but also various substances such as insectifuges, mildew-proofing agents and rust preventives may be formed into an inclusion compound so long as it can be included in cyclodextrin to thereby produce synthetic resin products having the effect of each substance.

However these inclusion compounds consisting of perfumes, insectifuges, mildew-proofing agents or rust preventives included in cyclodextrin can not be used in practice in synthetic resin products of a high molding temperature, i.e. 180° C. or above. Cyclodextrin per se is stable at high temperatures and shows no chemical change so that it is theoretically possible to use it in a synthetic resin of a high molding temperature. However pure cyclodextrin is so expensive that decomposed starches containing cyclodextrin are employed in practice. These decomposed starches contain reducing sugars which would be denatured and charred when molded at a high temperature.

Although there is no problem in the production of a synthetic resin product having various effects by forming an inclusion compound consisting of perfume(s), insectifuge(s) or rust preventive(s) included in cyclodextrin, drying and powdering the obtained inclusion compound and mixing the obtained powder with a synthetic resin compound on a laboratory scale with the use of pure cyclodextrin, there remains a problem to be solved in the production thereof on an industrial scale.

In addition, the volatility of each substance is somewhat depressed by including the same in cyclodextrin to thereby form an inclusion compound, which allows its effect to persist for a much longer period than with conventional products. However the persistence is somewhat insufficient yet.

SUMMARY OF THE INVENTION

Under these circumstances, the present invention provides a synthetic resin product containing a compound included in cyclodextrin and a process for the production of the same. The synthetic resin product according to the present invention contains an inclusion compound consisting of one or more substances selected from among perfumes, insectifuges, rust preventives, mildew-proofing agents and bactericides included in cyclodextrin and a glycitol wherein said perfume(s), insectifuge(s), rust preventive(s) and/or mildew-proofing agent(s) are inactivated by formulating into the inclusion compound in cyclodextrin and coated with said glycitol to thereby enhance the persistence of the effects thereof. The synthetic resin product exhibiting the abovementioned effects may be produced by mixing one or more substances selected from among perfumes, insectifuges, rust preventives, mildew-proofing agents and bactericides with a reduced cyclodextrin millet jelly optionally containing cyclodextrin or a reduced millet jelly containing cyclodextrin to thereby form an inclusion compound consisting of said perfume(s), insectifuge(s), rust preventive(s), mildew-proofing agent(s) and/or bactericide(s) included in cyclodextrin; drying and powdering the obtained material containing the inclusion compound; melting 1 to 60% by weight of the obtained powder together with a synthetic resin compound; pelletizing the molten mixture; and molding the obtained pellets optionally with an appropriate amount of the synthetic resin compound. Alternately one or more substances selected from among perfumes, insectifuges, rust preventives, mildew-proofing agents and bactericides are mixed with a reduced cyclodextrin millet jelly optionally containing cyclodextrin or a reduced millet jelly containing cyclodextrin to thereby form an inclusion compound consisting of perfume(s), insectifuge(s), rust preventive(s), mildew-proofing agent(s) and/or bactericide(s) included in cyclodextrin. Then the obtained material containing the inclusion compound is dried and powdered and 1 to 60% by weight of the resulting powder is mixed with a synthetic resin coating, a synthetic resin adhesive or a synthetic resin tackifier as it is, ie., without heating or under heating. Accordingly reducing sugars contained as impurities in the cyclodextrin decomposed starch are converted into chemically stable glycitols which are used to form an inclusion compound consisting of perfume(s), insectifuge(s), rust preventive(s) and/or mildew-proofing agent(s). Then the obtained inclusion compound is dried and powdered and the resulting powder is converted into a chemically stable form by mixing with various synthetic resin materials, synthetic resin coating, synthetic resin adhesive or synthetic resin tackifier thus enabling the use of various synthetic resin materials and prolonging the duration period of the effect of each substance by taking advantage of the glycitol coating.

BRIEF DESCRIPTION OF THE DRAWINGS

FIG. 1 is a graph which shows the amounts (%) of residual fenitrothion (Sumithion) in samples 1 and 2 determined with the initial amount thereof as 100, wherein ● and ○ refer to samples and 1 and 2, respectively.

DETAILED DESCRIPTION OF PREFERRED EMBODIMENTS

The reduced millet jelly used in the present invention is obtained by hydrolyzing starch with an acid or an enzyme to give a maltoligosaccharide mixture comprising glucose, maltose, maltotriose and similar compounds and hydrogenating the mixture in the presence of a nickel catalyst under elevated pressure. Thus reductive terminals of the reducing sugars are hydrogenated to give the corresponding glycitols. That is, glucose, maltose and maltotriose are converted into sorbitol, maltitol and maltotriitol, respectively, and lose their reductivity. Thus the D.E. (dextrose equivalent; the ratio of reducing sugars to the total solid matters) of the mixture turns to 0. Therefore the mixture becomes more stable to heat and shows little coloration caused by a reaction with amino radicals contained in amino acids or the like, i.e. aminocarbonyl reaction.

The reduced cyclodextrin millet jelly used in the present invention includes the abovementioned reduced millet jelly containing cyclodextrin. Since cyclodextrin exhibits no reductivity, the D.E. of the same is 0. In practice, the reduced cyclodextrin millet jelly can be obtained by catalytically reducing a millet jelly containing cyclodextrin, e.g. Celldex CH-20 or CH-30 mfd. by Nippon Shokuhin Kako K. K., in the manner as described above. The cyclodextrin contained therein shows no change by the above procedure but reducing sugars other than the cyclodextrin are reduced and converted into the corresponding glycitols.

Either natural or synthetic perfumes may be used in the present invention. Examples of natural perfumes are animal or vegetable perfumes such as lavender oil, citronella oil, rose oil, lemon oil and jasmin oil. Examples of synthetic perfumes are ethyl acetoacetate ($C_6H_{10}O_3$), acetophenone ($C_8H_8O$), anisic aldehyde ($C_8H_8O_2$), benzyl benzoate ($C_{14}H_{12}O_2$), amyl cinnamic aldehyde ($C_{14}H_{18}O$), methyl benzoate ($C_8H_8O_2$), ethyl isovalerate ($C_7H_{14}O_2$), ethyl vanillin ($C_9H_{10}O_3$), ethylene brassylate ($C_{15}H_{26}O_4$), ethyl formate ($C_3H_6O_2$), citronellyl formate ($C_{11}H_{20}O_8$), coumarin ($C_9H_6O_2$), cuminaldehyde ($C_{10}H_{12}O$), cinnamyl alcohol ($C_9H_{10}O$), geraniol ($C_{10}H_{18}O$), acetyl eugenol ($C_{12}H_{14}O_3$), citronellyl acetate ($C_{12}H_{22}O_2$), terpinyl acetate ($C_{12}H_{20}O_2$), benzyl acetate ($C_9H_{10}O_2$), isoamyl salicylate ($C_{12}H_{16}O_3$), benzyl salicylate ($C_{14}H_{13}O_3$), cyclamen aldehyde ($C_{13}H_{18}O$), citral ($C_{10}H_{16}O$), citronellol ($C_{10}H_{20}O$), tetrahydrolinalool ($C_{10}H_{22}O$), terpineol ($C_{10}H_{18}O$), vanillin ($C_8H_8O_3$), ethyl phenylacetate ($C_{10}H_{12}O_2$), heliotropin ($C_6H_6O_3$), musk ambrette ($C_{12}H_{16}O_5N_2$), p-methylacetophenone ($C_9H_{10}O$), methylionone ($C_{14}H_{22}O$), ethyl methyl phenylglycidate ($C_{12}H_{14}O_3$), l-menthol ($C_{10}H_{20}O$), butyric acid ($C_4H_8O_2$), linalool ($C_{10}H_{18}O$), linonene & dipentene ($C_{10}H_{16}$), rosephenone ($C_{10}H_9Cl_3O_2$) and rosinol ($C_{10}H_{20}O$).

The mildewproofing agents used in the present invention are those having an antibacterial and bactericidal effect. Examples of a substance which mainly serves as an antibacterial agent or a bactericide are chlorhexydine gluconate ($C_{22}H_{30}Cl_2N_{10}\cdot 2C_6H_{12}O_7$: 897.77), N-(fluorodichloromethylthio)phthalimide and α-bromocinnamaldehyde ($C_9H_2OBr$).

Examples of compounds mainly available as a mildew-proofing agent are as follows:

thiabendazole;

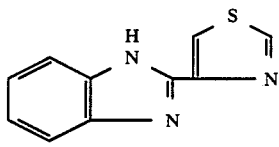

2-hydroxydiphenyl;

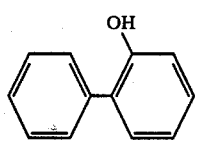

N-dimethyl-N'-phenyl-(N'-fluorodichloromethylthio)-sulfamide;

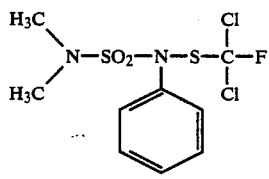

3-methyl-4-chlorophenol (p-chloro-m-cresol);

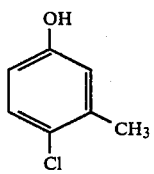

tolyltriazole (1H-4/5-methylbenzotriazole);

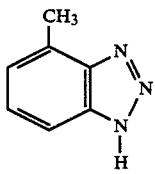

benzotriazole (1,2,3-benzotriazole);

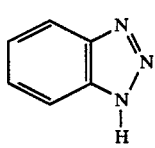

The insectifuges used in the present invention include not only repellents such as citronella oil but also those having an insectifugal and insecticidal effect. More particularly it is preferable to use organic phosphorus or pyrethroid insecticides.

An example of the organic phosphorus insecticide used in the present invention is fenitrothion (O,O-dimethyl ) O-(3-methyl-4-nitrophenyl)thiophosphorate;

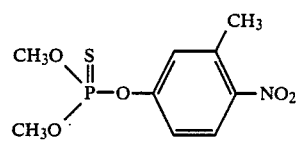

Examples of the pyrethroid insecticides are as follows.

allethrin [dl-3-allyl-2-methyl-4-oxo-2-cyclopentenyl dl-cis/trans-chrysanthemate];

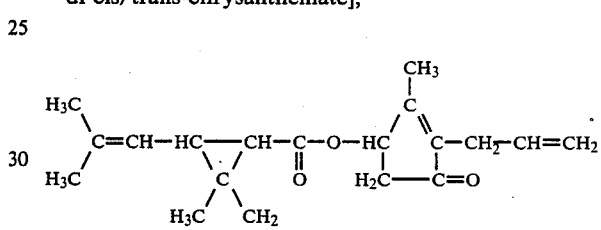

phthalthrin [(1,3,4,5,6,7-hexahydro-1,3-dioxo-2-isoindolyl)methyl dl-cis/trans-chrysanthemate];

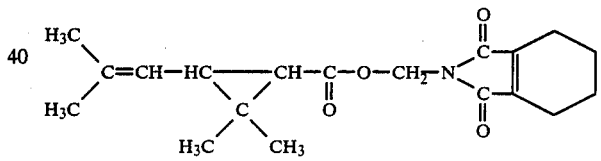

resmethrin [(benzyl-3-furyl)methyl dl-cis/trans-chrysanthemate];

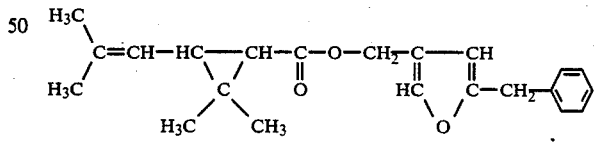

furamethrin [(5-(2-propinyl)-2-furyl)methyl dl-cis/trans-chrysanthemate];

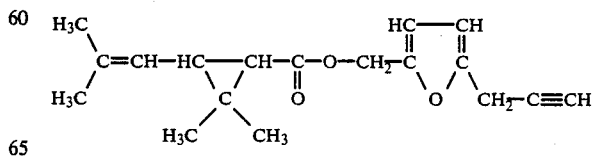

phenothrin [3-phenoxybenzyl d-cis/trans-chrysanthemate];

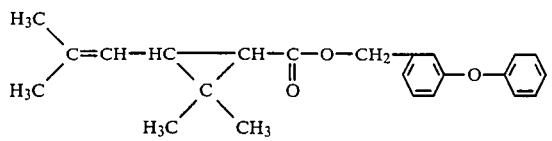

permethrin [3-phenoxybenzyl dl-cis/trans-3-(2,2-dichlorovinyl)-2,2-dimethyl-1-cyclopropanecarboxylate];

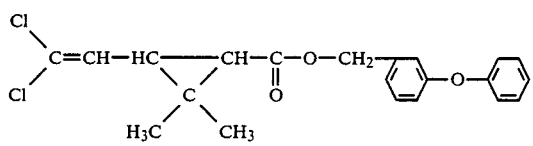

and
2-(4-ethoxyphenyl)-2-methylpropyl 3-phenoxybenzyl ether

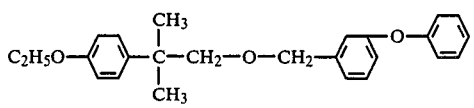

Organic phosphorus and pyrethroid insecticides are used as an insectifugal and insecticidal agents since they exhibit an excellent effect, a low toxicity and a high stability and are available in a wide range. Further they can be readily formulated into an inclusion compound in cyclodextrin. Furthermore they are so stable at high temperatures that they can be mixed with a synthetic resin compound for molding.

Any rust preventive such as liquid paraffin or spindle oil may be used in the present invention so long as they can be included in cyclodextrin. Volatile rust preventives or volatile rust preventive oils such as dicyclohexylammonium nitrite [$(C_6H_{10})_2NH_3HNO_2$], di-isopropylamine nitrite [$(CH_3)_2CH)_2NH.HNO_2$) (dipan)] and ferro-bright oil may be employed.

Any synthetic resin coating, synthetic resin tackifier and synthetic resin adhesive may be used in the present invention so long as they comprise synthetic resin(s). Examples thereof are synthetic rubbers, synthetic rubber adhesives and synthetic rubber tackifiers.

Examples of the synthetic resin coatings are alkyd resin coatings, amino alkyd resin coatings, vinyl resin coatings, acrylic resin coatings, epoxy resin coatings, polyurethane coatings and unsaturated polyester coatings.

Examples of synthetic resin adhesives are thermoplastic resin adhesives such as vinyl resin adhesives, acrylic resin adhesives, α-cyanoacrylate and tetraethylene glycol dimethacrylate and thermosetting resin adhesives such as phenol resin adhesives, resorcinol resin adhesives, xylene resin adhesives, furan resin adhesives, urea resin adhesives, melamine resin adhesives; epoxy resin adhesives and polyurethane adhesives.

Examples of the synthetic resin product containing a compound included in cyclodextrin according to the present invention and a process for the production of the same will now be described.

EXAMPLE 1

20 parts by weight of α-cyclodextrin and 65 parts by weight of a reduced millet jelly were added to 15 parts by weight of geraniol and the mixture was stirred at 70° C. for one hour to give a material which contained a molecular inclusion compound of geraniol in cyclodextrin. The obtained material was dried and ground in a vacuum drier at 60° C. to give a powder of 150 mesh or finer. 10 parts by weight of this powder was melted together with 90 parts by weight of polyethylene pellets and the molten mixture was pelletized by cold cut method. These pellets were injection molded to give cups, pen cases and toys having a smell of rose.

EXAMPLE 2

90 parts by weight of a reduced cyclodextrin millet jelly containing 20% by weight of cyclodextrin was added to 10 parts by weight of jasmin oil and the mixture was stirred at 70° C. for one hour to give a material containing a molecular inclusion compound of jasmine in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method. From the obtained pellets, a packaging film having smell of jasmine was produced by blown film extrusion.

EXAMPLE 3

20 parts by weight of β-cyclodextrin and 65 parts by weight of a reduced cyclodextrin millet jelly containing 20% of cyclodextrin were added to 15 parts by weight of coffee oil and the mixture was stirred at 65° C. for one hour to give a material containing a molecular inclusion compound of coffee oil in cyclodextrin. The obtained material was dried and ground in a spray drier at 80° C. to give a powder of 150 mesh or finer. 10 parts by weight of this powder was melted together with 90 parts by weight of a plasticized polyvinyl chloride molding compound. The molten mixture was pelletized by hot cut method. Then 20 parts by weight of the obtained pellets were mixed with 80 parts by weight of the plasticized polyvinyl chloride molding compound and the mixture was molded to make straws by extrusion.

EXAMPLE 4

10 parts by weight of β-cyclodextrin and 70 parts by weight of a reduced cyclodextrin millet jelly containing 20% of cyclodextrin were added to 20 parts by weight of dimethyl phthalate and the mixture was stirred at 70° C. for one hour to give a material containing a molecular inclusion compound of dimethyl phthalate in cyclodextrin. The obtained material was dried and ground in a spray drier at 80° C. to give a powder of 150 mesh or finer. 30 parts by weight of this powder was melted together with 70 parts by weight of polyethylene pellets. The molten mixture was pelletized by hot cut method. From the obtained pellets, a vermin-proof polyethylene film was produced by calendering.

EXAMPLE 5

20 parts by weight of β-cyclodextrin and 65 parts by weight of a reduced millet jelly were added to 15 parts by weight of fenitrothion and the mixture was stirred at 70° C. for one hour to give a material containing a molecular inclusion compound of fenitrothion in cyclodextrin. The obtained material was dried and ground in a vacuum drier at 60° C. to give a powder of 150 mesh or finer. 50 parts by weight of this powder was melted together with 50 parts by weight of a plasticized polyvinyl chloride molding compound. The molten mixture was pelletized by cold cut method. Then 10 parts by weight of the obtained pellets were mixed with 90 parts by weight of the plasticized polyvinyl chloride molding compound. From the resulting material, a pipe for use in the cultivation of plants was produced by extrusion molding.

EXAMPLE 6

20 parts by weight of β-cyclodextrin and 70 parts by weight of a reduced millet jelly containing 20% of cyclodextrin were added to 10 parts by weight of phthalthrin and the mixture was stirred at 65° C. for one hour to give a material containing a molecular inclusion compound of phthalthrin in cyclodextrin. The obtained material was dried and ground in a spray drier at 90° C. to give a powder of 150 mesh or finer. 30 parts by weight of this powder was melted together with 70 parts by weight of a plasticized polyvinyl chloride molding compound. The molten mixture was pelletized by hot cut method. Then 20 parts by weight of the obtained pellets were mixed with 80 parts by weight of the plasticized polyvinyl chloride molding compound. From the resulting material, a belt was molded by extrusion for use in growing tree.

EXAMPLE 7

85 parts by weight of a reduced cyclodextrin millet jelly obtained by reducing a decomposed starch containing 20% of α-, β- and γ-cyclodextrins was added to 15 parts by weight of resmethrin and the mixture was stirred at 70° C. for one hour to give a material containing a molecular inclusion compound of resmethrin in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method. From the obtained pellets, a flower pot was produced by injection.

EXAMPLE 8

80 parts by weight of a reduced cyclodextrin millet jelly obtained by reducing a decomposed starch containing 20% of α-, β- and γ-cyclodextrins and 5 parts by weight of β-cyclodextrin were added to 15 parts by weight of furamethrin and the mixture was stirred at 70° C. for one hour to give a material containing a molecular inclusion compound of furamethrin in cyclodextrin. The obtained material was dried and ground in a spray drier at 90° C. to give a powder of 150 mesh or finer. 10 parts by weight of this powder was melted together with 90 parts by weight of a polyvinyl acetate compound. The molten mixture was pelletized by underwater cut method. Then 20 parts by weight of the obtained pellets were mixed with 80 parts by weight of a polyvinyl acetate compound. From the resulting material, a bag for use in protecting fruits was produced by blown film extrusion.

EXAMPLE 9

80 parts by weight of a reduced cyclodextrin millet jelly containing 20% of cyclodextrin was added to 20 parts by weight of phenothrin and the mixture was stirred at 70° C. for one hour to give a molecular inclusion compound of phenothrine in cyclodextrin. The obtained inclusion compound was dried and ground in a drum drier at 130° C. to give a powder of 150 mesh or finer. 10 parts by weight of this powder was melted together with 90 parts by weight of an ethylene-vinyl acetate compound. The molten mixture was pelletized by sheet cutting from which a film was produced by extrusion.

EXAMPLE 10

85 parts by weight of a reduced cyclodextrin millet jelly obtained by reducing a decomposed starch containing 20% of α-, β- and γ-cyclodextrins was added to 15 parts by weight of permethrin and the mixture was stirred at 65° C. for one hour to give a material containing a molecular inclusion compound of permethrin in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method from which a square board was molded by injection, for cockroach avoiding.

EXAMPLE 11

10 parts by weight of β-cyclodextrin and 80 parts by weight of a reduced millet jelly were added to 10 parts by weight of allethrin and the mixture was stirred at 70° C. for one hour to give a material containing a molecular inclusion compound of allethrin in cyclodextrin. The obtained material was dried and ground in a spray drier at 90° C. to give a powder of 150 mesh or finer. 30 parts by weight of this powder was melted together with 70 parts by weight of a plasticized polyvinyl chloride molding compound. The molten mixture was pelletized by hot cut method. Then 20 parts by weight of the obtained pellets were mixed with 80 parts by weight of the plasticized polyvinyl chloride molding compound. From the resulting material, a lamp shade was produced by blow molding for mosquitoes killing/avoiding.

EXAMPLE 12

10 parts by weight of β-cyclodextrin and 75 parts by weight of a reduced millet jelly were added to 15 parts by weight of fenitrothion and the mixture was stirred at 70° C. for one hour to give a material containing a molecular inclusion compound of fenitrothion in cyclodextrin. The obtained material was dried and ground in a vacuum drier at 60° C. to give a powder of 150 mesh or finer. 50 parts by weight of this powder was melted together with 50 parts by weight of a plasticized polyvinyl chloride molding compound. The molten mixture was pelletized by cold cut method. Then 10 parts by weight of the obtained pellets were mixed with 90 parts by weight of the plasticized polyvinyl chloride molding compound and the resulting material was molded into a film by calender process.

EXAMPLE 13

At first, 5 parts by weight of camphur oil was added to 10 parts by weight of fenitrothion, and into this mixture, 10 parts by weight of β-cyclodextrin and 75 parts by weight of a reduced cyclodextrin millet jelly containing 20% of cyclodextrin were added, and the mixture was stirred at 70° C. for one hour to give a material containing a molecular inclusion compound of fenitrothion in cyclodextrin. The obtained material was dried and ground in a spray drier at 80° C. to give a powder of 150 mesh or finer. 30 parts by weight of this powder was melted together with 70 parts by weight of a plasticized polyvinyl chloride molding compound. The molten mixture was pelletized by hot cut method. Then 10 parts by weight of the obtained pellets were mixed with 90 parts by weight of the plasticized polyvinyl chloride molding compound and the resulting material was molded into a film by extrusion.

EXAMPLE 14

85 parts by weight of a reduced cyclodextrin millet jelly obtained by reducing a decomposed starch containing 20% of $\alpha$-, $\beta$- and $\gamma$-cyclodextrins was added to 15 parts by weight of allethrin and the mixture was stirred at 70° C. for one hour to give a material containing a molecular inclusion compound of allethrin in cyclodextrin. The obtained material was dried and ground in a vacuum drier at 60° C. to give a powder of 150 mesh or finer. 20 parts by weight of the obtained powder was melted together with 80 parts by weight of polyethylene pellets. The molten mixture was pelletized by cold cut method. The resulting pellets were molded into a film by calender process.

EXAMPLE 15

90 parts by weight of a reduced cyclodextrin millet jelly obtained by reducing a decomposed starch containing 20% by weight of $\alpha$-, $\beta$- and $\gamma$-cyclodextrins was added to 10 parts by weight of phthalthrin and the mixture was stirred at 70° C. for one hour to give a material containing a molecular inclusion compound of phthalthrin in cyclodextrin. The obtained material was dried and ground in a spray drier at 80° C. to give a powder of 150 mesh or finer. 10 parts by weight of this powder was melted together with 90 parts by weight of a polyvinyl acetate compound. The molten mixture was pelletized by underwater cut method. Then 30 parts by weight of the obtained pellets were mixed with 70 parts by weight of a polyvinyl acetate compound. The resulting mixture was molded into a film by extrusion.

EXAMPLE 16

5 parts by weight of $\alpha$-cyclodextrin and 75 parts by weight of a reduced millet jelly were added to 20 parts by weight of resmethrin and the mixture was stirred at 70° C. for one hour to give a material containing a molecular inclusion compound of resmethrine in cyclodextrin. The obtained mixture was dried and ground in a drum drier at 140° C. to give a powder of 150 mesh or finer. 10 parts by weight of this powder was melted together with 90 parts by weight of an ethylene-vinyl acetate compound. The molten mixture was pelletized by sheet cut method. The resulting material was molded into a film by extrusion.

EXAMPLE 17

5 parts by weight of $\beta$-cyclodextrin and 75 parts by weight of a reduced millet jelly were added to 20 parts by weight of liquid paraffin and the mixture was stirred at 70° C. for one hour to give a material containing a molecular inclusion compound of liquid paraffin in cyclodextrin. The obtained material was dried and ground in a spray dried at 90° C. to give a powder of 150 mesh or finer. 20 parts by weight of this powder was melted together with 80 parts by weight of polyethylene pellets. The molten mixture was pelletized by cold cut method. The resulting pellets were molded into a rust preventive film.

EXAMPLE 18

90 parts by weight of a reduced cyclodextrin millet jelly containing 20% of cyclodextrin was added to 10 parts by weight of spindle oil and the mixture was stirred at 70° C. for one hour to give a material containing a molecular inclusion compound of spindle oil in cyclodextrin. The obtained material was dried and ground in a spray drier at 90° C. to give a powder of 150 mesh or finer. 20 parts by weight of this powder was melted together with 80 parts by weight of polyethylene pellets. The molten mixture was pelletized by cold cut method. The resulting pellets were molded into a rust preventive film for packaging.

EXAMPLE 19

85 parts by weight of a reduced cyclodextrin millet jelly obtained by reducing a decomposed starch containing 20% of $\alpha$-, $\beta$- and $\gamma$-cyclodextrins was added to 15 parts by weight of thiavendazole and the mixture was stirred at 70° C. for one hour to give a material containing a molecular inclusion compound of thiavendazole in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method. The resulting pellets were molded into a film having a mold/mildew-proofing or anti-fungi effect by calender process.

EXAMPLE 20

90 parts by weight of a reduced cyclodextrin millet jelly obtained by reducing a decomposed starch containing 20% by weight of $\alpha$-, $\beta$- and $\gamma$-cyclodextrins was added to 10 parts by weight of 3-methyl-4-chlorophenol and the mixture was stirred at 70° C. for one hour to give a material containing a molecular inclusion compound of 3-methyl-4-chlorophenol in cyclodextrin. The obtained material was dried and ground in a spray drier at 90° C. to give a powder of 150 mesh or finer. 10 parts of weight of this powder was melted together with 90 parts by weight of a polyvinyl acetate compound. The molten mixture was pelletized by underwater cut method. Then 40 parts by weight of the obtained pellets were mixed with 60 parts by weight of the polyvinyl acetate compound and the resulting material was molded into a film having a mold/mildew-proofing or anti-fungi effect by extrusion.

EXAMPLE 21

85 parts by weight of a reduced cyclodextrin millet jelly obtained by reducing a decomposed starch containing 20% of $\alpha$-, $\beta$- and $\gamma$-cyclodextrins was added to 15 parts by weight of tolyltriazole and the mixture was stirred at 70° C. for one hour to give a material containing a molecular inclusion compound of tolyltriazole in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method. The resulting pellets were molded into a flower pot having a mold/mildew-proofing or anti-fungi effect by injection.

EXAMPLE 22

10 parts by weight of β-cyclodextrin and 80 parts by weight of a reduced millet jelly were added to 10 parts by weight of liquid paraffin and 10 parts by weight of benzotriazole and the mixture was stirred to 70° C. for one hour to give a molecular inclusion compound of liquid paraffin and benzotriazole included in cyclodextrin. The obtained material was dried and ground in a vacuum drier at 60° C. to give a powder of 150 mesh or finer. 20 parts by weight of this powder was melted together with 80 parts by weight of silicone resin. By the use of injection molding machine (mfd. by Sanjo-Seiki Co. Ltd.), the molten mixture was molded into a semiconductor substrate exhibiting a rust-preventive and mold/mildew-proofing or anti-fungi effect.

EXAMPLE 23

10 parts by weight of β-cyclodextrin and 60 parts by weight of a reduced millet jelly were added to 15 parts by weight of liquid paraffin and 15 parts by weight of 2-hydroxydiphenyl and the mixture was stirred at 70° C. for one hour to give a material containing a molecular inclusion compound of liquid paraffin and 2-hydroxydiphenyl in cyclodextrin. The obtained material was dried and ground in a spray drier at 80° C. to give a powder of 150 mesh or finer. 20 parts by weight of this powder was melted together with 80 parts by weight of epoxy resin. The molten mixture was pelletized. The resulting pellets were molded into a semiconductor substrate having a rust-preventive and mold/mildew-proofing or anti-fungi effect.

EXAMPLE 24

90 parts by weight of a reduced cyclodextrin millet jelly obtained by reducing a decomposed starch containing 20% by weight of α-, β- and γ-cyclodextrins was added to 10 parts by weight of 3-methyl-4-chlorophenol and the mixture was stirred at 70° C. for one hour to give a material containing a molecular inclusion compound consisting of 3-methyl-4-chlorophenol in cyclodextrin. The obtained material was dried and ground in a spray drier at 80° C. to give a powder of 150 mesh or finer. 10 parts by weight of this powder was mixed with 90 parts by weight of an alkyd resin coating to give a mold/mildew-proofing or anti-fungi coating.

EXAMPLE 25

85 parts by weight of a reduced cyclodextrin millet jelly obtained by reducing a decomposed starch containing 20% of α-, β- and γ-cyclodextrins was added to 15 parts by weight of tolyltriazole and the mixture was stirred at 70° C. for one hour to give a material containing a molecular inclusion compound of tolyltriazole in cyclodextrin. The obtained material was dried and ground in a vacuum drier at 60° C. to give a powder of 150 mesh or finer. 10 parts by weight of this powder was mixed with 90 parts by weight of a vinyl resin coating to give a mold/mildew-proofing or anti-fungi coating.

EXAMPLE 26

90 parts by weight of a reduced cyclodextrin millet jelly obtained by reducing a decomposed starch containing 20% by weight of α-, β- and γ-cyclodextrins was added to 10 parts by weight of phthalthrin and the mixture was stirred at 70° C. for one hour to give a material containing a molecular inclusion compound consisting of phthalthrin in cyclodextrin. The obtained material was dried and ground in a spray drier at 90° C. to give a powder of 150 mesh or finer. 10 parts by weight of this powder was mixed with 90 parts by weight of an acrylic resin adhesive to give a vermin-proofing adhesive.

EXAMPLE 27

85 parts by weight of a reduced cyclodextrin millet jelly obtained by reducing a decomposed starch containing 20% by weight of a α-, β- and γ-cyclodextrins was added to 15 parts by weight of allethrin and the mixture was stirred at 65° C. for one hour to give a material containing molecular inclusion compound of allethrin in cyclodextrin. The obtained material was dried and ground in a vacuum drier at 60° C. to give a powder of 150 mesh or finer. 10 parts by weight of this powder was mixed with 90 parts by weight of a phenol resin adhesive to give a vermin-proofing adhesive.

EXAMPLE 28

85 parts by weight of a reduced cyclodextrin millet jelly obtained by reducing a decomposed starch containing 20% of α-, β- and γ-cyclodextrins was added to 15 parts by weight of tolyltriazole and the mixture was stirred at 70° C. for one hour to give a material containing a molecular inclusion compound of tolyltriazole in cyclodextrin. The obtained material was dried and ground in a vacuum drier at 60° C. to give a powder of 150 mesh or finer. 10 parts by weight of this powder was mixed with 90 parts by weight of a urea resin adhesive to give a mold/mildew-proofing or anti-fungi adhesive.

EXAMPLE 29

85 parts by weight of a reduced cyclodextrin millet jelly obtained by reducing a decomposed starch containing 20% of α-, β- and γ-cyclodextrins was added to 15 parts by weight of 2-(4-ethoxyphenyl)-2-methylpropyl 3-phenoxybenzyl ether and the mixture was stirred at 70° C. for one hour to give a material containing a molecular inclusion compound of 2-(4-ethoxyphenyl in cyclodextrin. The obtained material was dried and ground in a vacuum drier at 60° C. to give a powder of 150 mesh or finer. 20 parts by weight of this powder was melted together with 80 parts by weight of polyethylene pellets. The molten mixture was pelletized by cold cut method. The resulting pellets were molded into a bactericidal film by calender process.

EXAMPLE 30

90 parts by weight of a reduced cyclodextrin millet jelly obtained by reducing a decomposed starch containing 20% by weight of α-, β- and γ-cyclodextrins was added to 10 parts by weight of α-bromocinnamaldehyde and the mixture was stirred at 70° C. for one hour to give a material containing a molecular inclusion compound consisting of α-bromocinnamaldehyde in cyclodextrin. The obtained material was dried and ground in a spray drier at 90° C. to give a powder of 150 mesh or finer. 10 parts by weight of this powder was mixed with 90 parts by weight of an acrylic resin adhesive to give a bacteria-proofing or anti-fungi adhesive.

EXAMPLE 31

20 parts by weight of a mold/mildew-proofing and bacteria-proofing agent N-(flurodichloromethylthio)phthalimide (Preventol A3; mfd. by Bayer Co., Ltd.) dissolved in acetone, 20 parts by weight of α-cyclodextrin and 60 parts by weight of mannitol (or xylitol) were mixed and the mixture was stirred at 65° C. in a conventional manner to give a molecular inclusion compound. The obtained inclusion compound was powdered in a spray drier. 10% of this powder was added to an acrylic emulsion coating to give an emulsion coating having an excellent mold/mildew-proofing and anti-fungi effect.

EXAMPLE 32

An unmodified liquid epoxy resin (Epikote; mfd. by Shell Chemicals Co., Ltd.) was included in cyclodextrin to form a molecular inclusion compound which was then powdered at a low temperature drying. A polyolefinic polymer powder (Dumiran; mfd. by Takeda Chemical Industries Co., Ltd.) was mixed with the above cyclodextrin powder in a ratio of 3:1 and the mixture was pelletized by the use of a special pelletizer and stored at room temperature. This product was used in hot-melt coating with a coating machine at an arbitrary time at a temperature of 90° to 120° C. Thus an excellent adhesion accompanied by crosslinkage was facilitated. Conventional nonincluded adhesives must be stored at lower temperature but the product as described above can be stored at room temperature without showing any crosslinkage, which is highly advantageous.

COMPARATIVE EXAMPLE 1

A vermin-proofing and insecticidal film containing fenitrothion produced in a conventional manner (hereinafter referred to as sample 1) and another vermin-proofing and insecticidal film containing fenitrothion and produced by the process of the present invention (hereinafter referred to as sample 2) were prepared. Each film was allowed to stand at 25° C. and the change in the amount of fenitrothion contained therein was monitored by high performance liquid chromatography. Samples 1 and 2 were as follows.

Sample 1: Fenitrothion (Sumithion; mfd. by Sumitomo Chemical Co., Ltd.) was included in a millet jelly containing cyclodextrin (Celldex CH-20; mfd. by Nippon Shokuhin Kako K. K. and containing 20% by cyclodextrin). The obtained molecular inclusion compound was mixed with polyethylene pellets and the mixture was molded into a film by inflation process.

Sample 2: This sample is a product of the present invention. The same procedure as described relating to the above sample 1 was followed to prepare film, except that the millet jelly containing cyclodextrin was substituted by hydrogenated millet jelly containing cyclodextrin (tentatively named 20H).

The following table shows the amounts (%) of residual fenitrothion (Sumithion) in samples 1 and 2 determined with the initial amount of the same as 100%. FIG. 1 shows changes in the residual amounts (%) thereof determined with the initial amount of the same as 100%, wherein ● and ○ refer to samples 1 and 2, respectively.

The table and FIG. 1 clearly suggest that sample 2 can repress the volatilization of Sumithion (i.e. a guest compound) by approximately 20% compared with sample 1. Thus the present invention makes it possible to decrease the necessary amount of the guest compound as well as to prolong the duration period of the effect of the same. It has further proved that the present invention can prolong the duration periods of the effects of insecticides other than Sumithion, perfumes, mold/mildew-proofing or anti-fungi agents and rust preventives.

TABLE

| Days | Sample 1 mg/g · sheet | % | Sample 2 mg/g · sheet | % |
| --- | --- | --- | --- | --- |
| 0 | 2.31 | 100.0 | 2.45 | 100.0 |
| 5 | 2.01 | 87.0 | 2.27 | 92.7 |
| 15 | 1.83 | 79.2 | 2.05 | 83.7 |
| 30 | 1.31 | 56.7 | 1.88 | 76.7 |
| 45 | 1.25 | 54.1 | 1.60 | 65.3 |
| 55 | 1.21 | 52.2 | 1.59 | 64.9 |
| 65 | 1.20 | 51.8 | 1.57 | 64.1 |
| 75 | 1.16 | 50.3 | 1.56 | 63.7 |
| 85 | 1.12 | 49.9 | 1.54 | 62.9 |
| 95 | 1.08 | 46.8 | 1.53 | 62.4 |
| 105 | 1.05 | 45.8 | 1.53 | 62.4 |
| 115 | 1.03 | 44.6 | 1.50 | 61.2 |
| 125 | 1.01 | 43.7 | 1.49 | 60.6 |

COMPARATIVE EXAMPLE 2

Samples 3, 4 and 5 were produced by the following manner and thermal stability, dispersibility and compatibility of each sample were examined.

SAMPLE

Sample 3: A perfume was included in a millet jelly containing cyclodextrin (Celldex CH-20; mfd. by Nippon Shokuhin Kako K. K. and containing 20% of cyclodextrin) to form a molecular inclusion compound which was then molded into master pellets. 10 parts by weight of these master pellets were mixed with 90 parts by weight of polyethylene pellets and the mixture was molded into a film of 100μ in thickness by inflation.

Sample 4: This sample is a product of the present invention. A film was produced in the same manner as described relating to the above sample 3 except that the millet jelly containing cyclodextrin was substituted by a hydrogenated millet jelly containing cyclodextrin (Celldex CH-20 H; mfd. by Nippon Shokuhin Kako K. K. and containing 20% of cyclodextrin).

Sample 5: A film was produced in the same manner as described relating to the above sample 3 except that the millet jelly containing cyclodextrin was substituted by β-cyclodextrin.

THERMAL STABILITY

Sample 3 showed no trouble at molding temperature of 150° to 170° C. but sugars contained therein were charred and colored at 200° C. accompanied by a burning smell.

Sample 4 showed no change at the molding temperature (200° C.). It was confirmed that it can be molded at a higher temperature than sample 3.

Sample 5 showed no trouble at the molding temperature (200° C.) similar to sample 4.

DISPERSIBILITY AND COMPATIBILITY

Sample 3 showed an excellent dispersibility and an excellent compatibility.

Sample 4 showed an excellent dispersibility and an excellent compatibility.

Sample 5 showed a much worse compatibility than those of samples 3 and 4. The dispersibility of its inclusion compound was also poor.

DISCUSSION

Sample 3 showed an excellent dispersibility as well as an excellent compatibility but the thermal stability thereof was poor. Sample 5 showed an excellent thermal stability but the dispersibility and compatibility thereof were poor. On the other hand, sample 4, which was the product of the present invention, showed an excellent thermal stability, an excellent dispersibility and excellent compatibility.

As described above, a synthetic resin product containing a compound included in cyclodextrin and a process for the production in cyclodextrin and a process for the production of the same according to the present invention, wherein perfume(s), insectifuge(s)/insecticide(s), mold/mildew-proofing or anti-fungi agent(s), rust preventive(s) and/or bactericide(s) are included in cyclodextrin to form a molecular inclusion compound which is then mixed with a synthetic resin compound and glycitol(s) to thereby produce a synthetic resin product, show a uniform effect caused by the uniform dispersion of the perfume(s), insectifuge(s)/insecticide, mold/mildew-proofing or anti-fungi agent(s) and/or bactericide(s) and an excellent thermal stability which makes it possible to mold the product at a higher temperature since reducing sugars contained in the decomposed starch as impurities are converted into glycitols. Further the glycitols exert an effect of significantly prolonging the duration periods of the effects of the various ingredients.

What is claimed is:

1. A synthetic resin product comprising a thermoplastic of thermosetting synthetic resin, cyclodextrin, glycitol and a molecular inclusion compound included in the cyclodextrin, said molecular inclusion compound being one or more substances selected from the group consisting of perfumes, insectifuges/insecticides, mold/mildew proofing agents, anti-fungi agents and bactericides.

2. A synthetic resin product as set forth in claim 1, wherein said synthetic resin is an olefin resin.

3. A synthetic resin product as set forth in claim 1, wherein said synthetic resin is a vinyl chloride resin.

4. A synthetic resin product as set forth in claim 1, wherein said synthetic resin is an epoxy resin.

5. A synthetic resin product as set forth in claim 1, wherein said synthetic resin is a silicone resin.

6. A synthetic resin product as set forth in claim 1, wherein said synthetic resin is a thermosetting resin.

7. A synthetic resin product as set forth in claim 1, wherein the molecular inclusion compound included in the cyclodextrin is coated by the glycitol.

8. A synthetic resin product as set forth in claim 1, wherein the glycitol comprises a reduced millet jelly.

9. A synthetic resin product as set forth in claim 1, wherein the glycitol comprises a reduced cyclodextrin millet jelly.

* * * * *